United States Patent [19]

Rubey et al.

[11] Patent Number: 5,846,293
[45] Date of Patent: Dec. 8, 1998

[54] METHOD FOR ADMITTING AND RECEIVING SAMPLES IN A GAS CHROMATOGRAPHIC COLUMN

[75] Inventors: Wayne A. Rubey, Vandalia; Richard C. Striebich, Dayton, both of Ohio

[73] Assignee: The University of Dayton, Dayton, Ohio

[21] Appl. No.: 851,888

[22] Filed: May 6, 1997

Related U.S. Application Data

[60] Provisional application No. 60/016,977 May 6, 1996.

[51] Int. Cl.⁶ .................................................. B01D 15/08
[52] U.S. Cl. ................................ 95/87; 95/82; 73/23.26; 73/23.27
[58] Field of Search ............................ 73/23.26, 23.27, 73/23.35; 95/82, 87, 89; 96/101–103

[56] References Cited

U.S. PATENT DOCUMENTS

| | | | |
|---|---|---|---|
| 4,923,486 | 5/1990 | Rubey | 55/67 |
| 4,976,750 | 12/1990 | Munari | 95/82 X |
| 5,028,243 | 7/1991 | Rubey | 55/67 |
| 5,048,322 | 9/1991 | Hiller et al. | 73/23.41 |
| 5,133,859 | 7/1992 | Frank et al. | 96/102 X |
| 5,141,532 | 8/1992 | Sacks et al. | 55/67 |
| 5,215,556 | 6/1993 | Hiller et al. | 95/87 |
| 5,545,252 | 8/1996 | Hinshaw et al. | 96/102 X |
| 5,642,278 | 6/1997 | Wang et al. | 96/102 X |
| 5,711,786 | 1/1998 | Hinshaw | 96/102 X |

OTHER PUBLICATIONS

Expanded Utilization of Analytical Separation Technologies, W.A. Rubey, *HRC*, 16 (1993), 453.

A Different Operational Mode for Addressing the General Elution Problem in Rapid Analysis Gas Chromatography, W.A. Rubey, *HRC*, 14 (1991) 542.

Operational Theory and Instrumental Implementation of the Thermal Gradient Programmed Gas Chromatography (TGPGC) Mode of Analysis, W.A. Rubey, *HRC*, 15 (1992) 795.

An Instrumentation Assembly for Studying Operational Behavior of Thermal Gradient Programmed Gas Chromatography, W.A. Rubey, *Rev. Sci. Instrum*, 65 (1994) 2802.

On–line Liquid Backflush of an Uncoated Precolumn for Automated Gas Chromatographic Analysis of Complex Mixtures, *Journal of Chromatography A*, 654 (1993) 287–298.

(List continued on next page.)

*Primary Examiner*—Robert Spitzer
*Attorney, Agent, or Firm*—Killworth, Gottman, Hagan & Schaeff, LLP

[57] ABSTRACT

A method of admitting and receiving a sample into a gas chromatographic column is provided in which a step increase in pressure is performed in combination with the application of a negative axial thermal gradient to provide pre-separation of solutes in the sample within the inlet region of the column. The method includes the steps of introducing a sample into the column at a first pressure and temperature, rapidly raising the temperature to invoke a negative axial thermal gradient, and then substantially instantaneously increasing the pressure. The method causes the solutes in the sample to be partially separated into narrow zones within the inlet region, resulting in eventually achieving maximum resolution.

8 Claims, 4 Drawing Sheets

OTHER PUBLICATIONS

Step Increase of the Carrier Gas Inlet Pressure in Gas Chromatography, Jacob et al., *Nature,* 213: 491–491 (1967).

The Effects of Column Temperature and Various Imposed Thermal Fields Upon Gas Chromatographic Resolution, W.A. Rubey, Presentation at Pittsburge Conference, New Orleans (1992).

Recent Activities in the Development of Thermal Gradient Programmed Gas Chromatography (TGPGC), W.A. Rubey, Presentation at Ohio Valley Chromatography Symposium, Hueston Woods, Ohio (1992).

Analytical Separations Performed Using the Thermal Gradient Programmed Gas Chromatography (TGPGC) Mode of Operation, R.C. Striebich and W.A. Rubey, Presenation at International Symposium on Capillary Chromatography, Baltimore (1992).

Progress in the Development of Thermal Gradient Programmed Gas Chromatography (TGPGC), W.A. Rubey, Presentation at Ohio Valley Chromatography Symposium, Hueston Woods, Ohio (1993).

An Introduction to Thermal Gradient Programmed Gas Chromatography, W.A. Rubey, Presentation at FACSS Meeting, Detroit (1993).

Rapid Analysis Performed Using Thermal Gradient Programmed Gas Chromatography, R.C. Striebich and W.A. Rubey, Presentation at FACSS Meeting, Detroit (1993).

Progress in the Development of Thermal Gradient Programmed Gas Chromatography (TGPGC) for High–Temperature Operation, W.A. Rubey, Presentation at Pittsburgh Conference, Chicago (1994).

Resolution Generation in Thermal Gradient Programmed Gas Chromatography (TGPGC), W.A. Rubey, Presentation at International Symposium on Capillary Chromatography and Electrophoresis, Wintergreen (1995).

Thermal Gradient Programmed Gas Chromatography: An Alternative Operational Mode for Conducting GC and GC–MS Analyses, W.A. Rubey, Presentation at National Research Council of Canada, Halifax, Nova Scotia (1991).

Thermal Gradient Programmed Gas Chromatography, W.A. Rubey, Presentation given at Wright State University Seminar Series (1991).

Rapid Chromatographic Detection of Explovisves, W.A. Rubey and R.C. Striebich, A White Paper for Federal Aviation Administration, Washington (1994).

Theoretical Aspects Pertaining to High–Temperature Operation of Thermal Gradient Programmed Gas Chromatography (TGPGC), W.A. Rubey, Invited Lecture, International Symposium on Capillary Chromatography, Riva del Garda (1994).

Futuristic Health Care and Separation Science, W.A. Rubey, Presentation given at Consiglio Nazionale Delle Ricerche in Bari (1994).

Rapid Separation of Complex Wide–Molecular–Weight Range Samples Using Thermal Gradient Programmed Gas Chromatography (TGPGC), W.A. Rubey and R.C. Striebich, Invited Paper, International Symposium on Capillary Chromatography and Electrophoresis, Wintergreen (1995).

The Implementation of Time–Programmed 3–and 4–Dimensional Fields Upon Open Tubular Gas Chromatography Columns, W.A. Rubey, Presentation at Rocky Mountain Conference on Analytical Chemistry, Denver (1990).

A Different Operational Mode for Conducting Gas Chromatographic Analyses, W.A. Rubey, Presentation at Ohio Valley Chromatography Symposium, Hueston Woods, Ohio (1991).

Instrumental Factors Associated with Implementing the Thermal Gradient Programmed Gas Chromatography (TGPGC) Mode of Operation, W.A. Rubey, Presentation at Pittsburgh Conference, Atlanta (1993).

Recent Theoretical and Experimental Developments Associated with Thermal Gradient Programmed Gas Chromatography (TGPGC), W.A. Rubey, Presentation at International Symposium of Capillary Chromatography, Riva de Garda (1993).

Theoretical Aspects Associated with High–Temperature Operation of Thermal Gradient Programmed Gas Chromatography (TGPGC), W.A. Rubey, Presentation at International Symposium on Capillary Chromatography, Riva de Garda (1994).

METHOD FOR ADMITTING AND RECEIVING SAMPLES IN A GAS CHROMATOGRAPHIC COLUMN

GOVERNMENT RIGHTS

The government has rights in the invention pursuant to Contract No. F33615-92-C-2218 awarded by the U.S. Air Force.

CROSS-REFERENCE TO RELATED APPLICATION

This application claims the benefit of U.S. provisional application Ser. No. 60/016,977 filed May 6, 1996.

BACKGROUND OF THE INVENTION

The present invention relates to an improved method for admitting and receiving samples in a gas chromatograph. More particularly, the invention relates to a method which utilizes a step-increased pressurization process in combination with the introduction of a thermal gradient at the inlet region of a gas chromatographic column in order to provide pre-separation of solutes in a sample within the inlet region and achieve optimum resolution.

Gas chromatography was first introduced in 1951 and has evolved into one of the most widely used instrumental chemical analysis techniques for separating sample mixture components. More than 300,000 gas chromatography instruments have been placed in operation. The two most widely practiced operational modes of gas chromatography have been isothermal gas chromatography (ITGC) and programmed-temperature gas chromatography (PTGC). Isothermal gas chromatography operates under constant temperature, and is generally used to analyze samples containing a relatively narrow molecular mass range. Programmed-temperature gas chromatography operates with a programmed increase in temperature as a function of time, and is generally preferred when analyzing complex organic mixtures which contain constituents having a wide range of molecular weights. However, neither isothermal nor programmed-temperature gas chromatography methods have provided pre-separation of sample components, i.e., the formation of partially separated individual zones in the front end of the column. The formation of narrow elution zones in gas chromatography is particularly desirable as it results in optimum resolution. Further, programmed-temperature gas chromatography separations are often time-consuming, particularly if they are performed with the use of open tubular columns which are extensive in length.

One method which has been proposed to reduce analysis time in gas chromatographic separations is the implementation of an instantaneous increase in the carrier gas inlet pressure when a sample is introduced into the inlet region of a column, referred to as a step increase in pressure. See Jacob et al, "Step Increase of the Carrier Gas Inlet Pressure in Gas Chromatography", Nature, Feb. 4, 1967, pp. 491–492. The step increase in pressure results in an acceleration of the carrier gas velocity and accelerates analysis of the sample, thus effectively reducing analysis time. However, such a method is limited to isothermal gas chromatography and thus is not practical for the separation of complex wide molecular weight range samples.

Another operational mode which has been developed in recent years for performing separations of complex mixtures is thermal gradient programmed gas chromatography (TGPGC). TGPGC utilizes an open tubular column, which has rapid thermal compliance due to its extremely thin walls. TGPGC separations operate by invoking a declining axial temperature gradient along the length of the column in three-dimensional (distance-temperature-time) fields. This method has been shown to allow quicker separation of complex samples than ITGC and PTGC methods. U.S. Pat. Nos. 4,923,486 and 5,028,243 to Rubey describe an example of a TGPGC separation in which a sample is introduced at a high temperature into an open tubular column such that a curvilinearly-shaped negative temperature gradient is imposed along the length of the column. The temperature gradient provides a smooth temperature decline along the length of the column as the sample travels from the injector end of the column to the detector end, and provides some pre-separation of components in the front end or inlet region of the column. However, while this method produces an efficient separation of complex samples with respect to time, the method is limited by the lack of formation of narrow elution zones in the inlet region of the column, and thus does not provide optimum resolution.

Another problem with current gas chromatographic methods is the formation of deposits of non-volatile or low molecular weight materials in the entrance region of the column which occurs when analyzing samples which contain components having a wide range of molecular weight such as environmental samples, petrochemical samples, hydrocarbon fuels and combustion by-products, and thermally labile samples such as pesticides. This deposit formation affects resolution of the samples, and over time, adversely affects the useful life of the gas chromatographic column. Although backflushing techniques have been introduced for cleaning the inlet region, such techniques generally have to be performed offline. Thus, deposit formation within injectors or open tubular columns has remained a problem.

Accordingly, there is still a need in the art for an improved method for admitting and receiving samples into a gas chromatographic column which provides short analysis time, which allows pre-separation of the components into narrow elution zones to provide good resolution, and which may be performed using a wide variety of samples. There is a further need in the art for an improved method of backflushing in the inlet region which prevents or minimizes the formation of deposits in the column.

SUMMARY OF THE INVENTION

The present invention meets those needs by providing a method for admitting and receiving samples into a gas chromatographic column which combines the application of step-increased pressurization along with thermal gradient programmed gas chromatography. The method results in improved pre-separation of sample solutes into narrow elution zones within the inlet region, faster analysis time, and high resolution. The method is gentle and may be used with samples of a gaseous, volatile, semi-volatile, or complex multi-phase nature containing a wide-molecular mass range. In addition, the method allows the inlet region of the column to be easily backflushed online to prevent the formation of deposits in the inlet region of the column.

According to one aspect of the invention, a method is provided for admitting and receiving a sample into a gas chromatograph column having an inlet region and an outlet region, where the sample travels in a forward direction from the inlet region to the outlet region. The method preferably comprises the step of admitting a sample into the inlet region of the column at a first temperature, where the inlet region contains a carrier gas which is at a first pressure, and then rapidly heating the inlet region to a second temperature greater than the first temperature such that a negative axial thermal gradient is imposed along the length of the column. After the inlet region is heated to the second temperature, the gas pressure at the inlet region is substantially instantaneously increased to a second pressure greater than the first pressure such that the velocity of the carrier gas is increased and the components of the sample (also termed "solutes") are pre-separated into narrow zones along the inlet region of the column. The velocity of the carrier gas is preferably increased to a velocity of about 5 m/s.

The column used in the present invention is preferably an open tubular column which may be constructed of fused silica or metal. By inlet region, it is meant the front end of the column where the sample is admitted and received. This region is from preferably about 20 cm to 2 meters in length.

Preferably, the sample is admitted to the column at a first pressure from between about 1 to 3 abs. atm (1.03 to 3.1 kg/cm$^2$) and a temperature of about 20° C. (close to room temperature). The inlet region is then preferably heated to a second temperature which is preferably between about 380° C. to 480° C., and is increased to a second pressure which is preferably between about 6 to 9 abs. atm (6.18 to 9.27 kg/cm$^2$).

The method of the present invention may further include the step of backflushing the inlet region of the column after pre-separation occurs. This is achieved by increasing the flow of gas pressure in the inlet region in a backward direction such that non-volatile materials in the sample which may have been deposited in the inlet region are removed from the inlet region. This backflushing step may be performed online after each pre-separation, which prevents the formation of deposits and eliminates the need for frequent maintenance of the injector/inlet region.

The step-increased pressurization method of the present invention results in high resolution due to the formation of narrow elution zones in the inlet region, while the application of a thermal gradient allows a wide variety of samples to be analyzed.

Accordingly, it is a feature of the invention to provide a method for admitting and receiving gas chromatographic samples which provides short analysis time, good resolution, and which may be performed using a wide variety of samples. It is a further feature of the invention to provide a method which allows on-line backflushing of the inlet region, eliminating the need for frequent injector-region maintenance. These, and other features and advantages of the present invention will become apparent from the following detailed description, the accompanying drawings, and the appended claims.

DETAILED DESCRIPTION OF THE PREFERRED EMBODIMENT

The method of the present invention improves the sample admission and reception process by utilizing, in combination, a step-increased pressurization and the application of an axial thermal gradient, which together function to accelerate the components of a sample such that significant pre-separation of the components occurs in narrow zones within the inlet region of a gas chromatographic open tubular column. This provides a significant advantage over prior art processes which do not pre-separate components, or which do not provide the formation of narrow solute zones.

The method of the present invention also permits the inlet region to be readily backflushed after each separation, minimizing or eliminating the problem of deposit formation. In addition, the method of the present invention can be performed with practically any type of open tubular column assembly.

Figure 1:
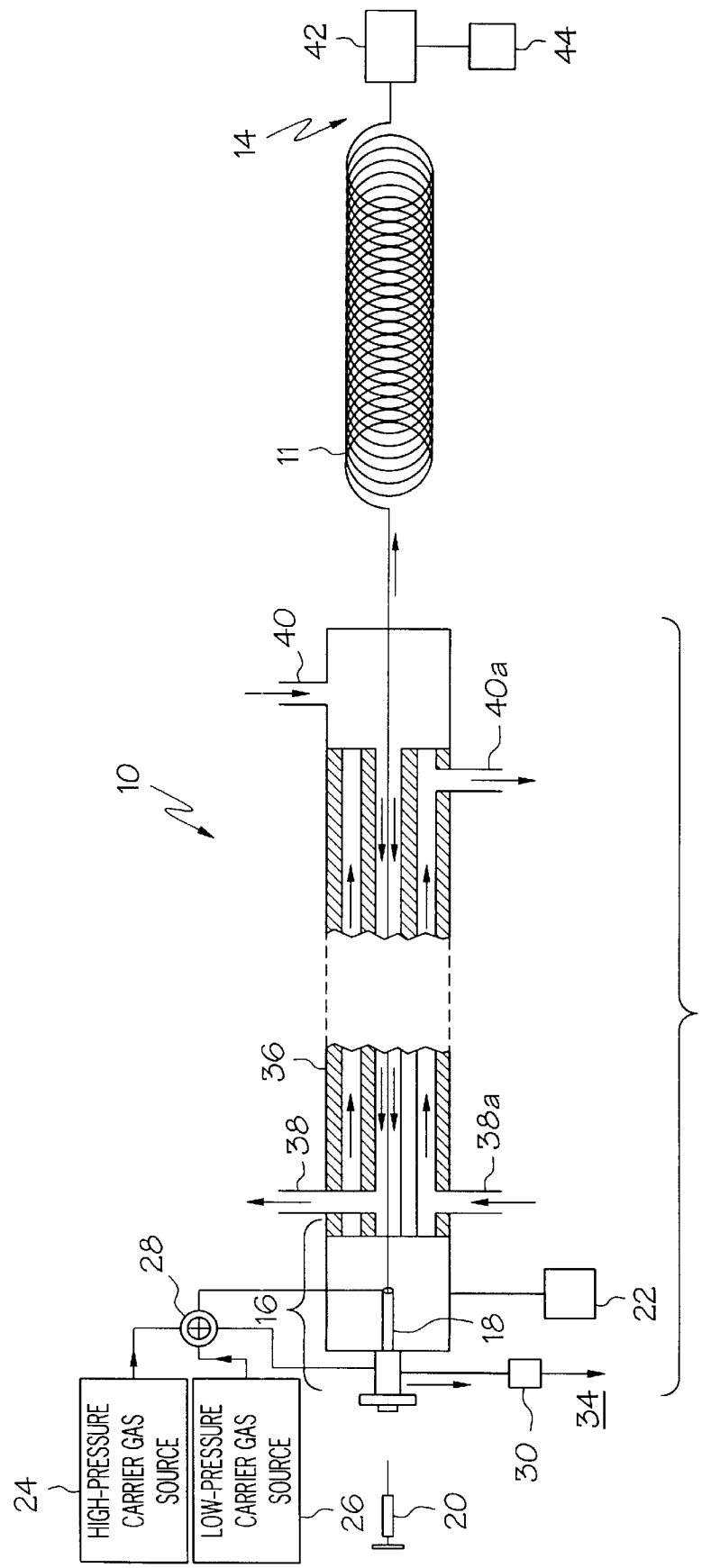
FIG. 1 is a schematic drawing, partially in section, of an open tubular column gas chromatograph which may be used in conjunction with the method of the present invention.

Referring now to the drawings, FIG. 1 is a schematic illustration of an open tubular column gas chromatograph which may be used to practice the method of the present invention. It should be appreciated that many variations of this chromatograph may be used with the method of the present invention.

The chromatograph 10 includes an open tubular column 11 which may vary in length. Depending on the desired application, the length of the column may be anywhere from 5 meters to 150 meters in length. The column may be comprised of fused silica or metal. Metal columns having a fused silica lining are preferred for use in the present invention as they can be heated more rapidly by a variety of heating techniques.

The chromatograph includes an inlet region 12 (also referred to as the reception region) and an outlet region 14. The inlet region may vary in length, depending on the length of the column. For example, the length of the inlet region may be only 20 cm for a short column, but may be up to 2 meters for a long column. The inlet region further includes an injection region 16 including an injector insert 18 where a sample is first introduced into the column, preferably by a syringe 20.

A heater 22 is preferably located adjacent to injection region 16 to create the desired thermal gradient after the sample is introduced into the column. A preferred heat source for use in the present invention is a high temperature air heater available from Convectronics Inc. of Methven, Mass. This heater may be controlled with a variable voltage source or with automatic temperature controls. Other suitable heat sources which may be used in the present invention include heat exchangers which are heated by electrical resistance or convection.

Sources of high and low pressure carrier gases 24, 26 are also provided to the injection region 16 which is controlled by a rapid actuation switching valve 28. A number of inert carrier gases may be used to introduce the sample to the inlet region including nitrogen, hydrogen and helium. Helium is preferred for use in the present invention.

The injection region 16 of the inlet region 12 preferably further includes a backflushing mechanism which includes a variable restrictor 30 and a backflush vent 34.

The inlet region 12 of the column further includes a double cylindrical conduit sleeve 36 which houses a portion of the front end of the column. The front portion of the sleeve includes inlet and exit gas ports 38a and 38 which circulate a fluid such as (heated) flow-controlled air or nitrogen gas through the sleeve. The rear portion of the sleeve includes inlet gas port 40 which admits (cold) flow-controlled air or nitrogen gas, and an exit gas port 40a.

A detector 42 is provided at the outlet region 14 of the open tubular column 11 which may be connected to a recorder 44 which is used to provide a chromatogram after a sample has been separated.

Figure 2:
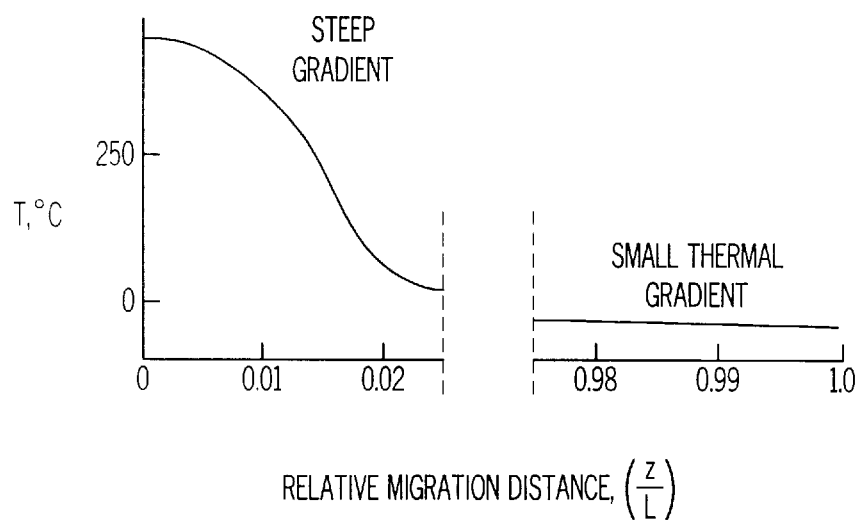
FIG. 2 is a graph of temperature (° C.) versus relative migration distance (z/L, where z is the distance traveled and L is the length of the column, both in meters) illustrating a typical axial thermal gradient applied to the column.

In the method of the present invention, a sample (typically containing a mixture of organic compounds) is injected into the inlet region 12 of open tubular column 11 using syringe 20. The sample travels through injector insert 18 and enters injection region 16 containing a carrier gas supplied from carrier gas source 26 at a low pressure of preferably about 1.2 atmospheres (1.24 kg/cm$^2$). The sample is preferably admitted to the injector region of the column at ambient temperature. The injector 16 is then rapidly heated by heater 22, preferably to a temperature of between about 380° C. and 480° C., which invokes a negative axial thermal gradient along the length of the column (i.e., the temperature gradient decreases as the solutes in the sample migrate along the column). FIG. 2 illustrates an example of a typical axial thermal gradient which may be applied. As shown, FIG. 2 illustrates a relatively steep thermal gradient applied at the inlet portion of the column which thermal gradient decreases along the remaining length of the column until it is relatively small at the exit end of the column.

Returning now to FIG. 1, after the sample has been admitted to the column and heated, the rapid actuation switching valve 28 is switched to high pressure gas source 24 such that the sample receives a substantially instantaneous step-increase in pressurization to about 8.0 absolute atmospheres (8.24 kg/cm$^2$). By "step-increased pressurization", it is meant that a substantially instantaneous increase in pressure occurs from a low (but positive) pressure to a substantially higher pressure in a short amount of time (about 30 milliseconds). For example, low-pressure carrier gas from source 26 may be at 1.2 atm (1.24 kg/cm$^2$) and high pressure carrier gas from source 24 may be at 8.0 atm (8.24 kg/cm$^2$) to provide a rate of increase in pressure of greater than about 220 atm/sec (~230 kg/cm$^2$/sec). This higher pressure may be referred to as the equilibrium migration pressure, meaning that this pressure provides optimum carrier velocity to the gas in the column. It should be appreciated that the low and high pressures applied may vary depending on the diameter of the column or the column length.

For the first few seconds after the step-increased pressurization, a surge in carrier gas velocity occurs. For example, while the carrier velocity may be initially only about 20 cm/sec when the sample is introduced, after the step-increase in pressure, mobile-phase velocities of up to 5 m/sec may be experienced.

In this step, the column acts like a pneumatic spring in that a velocity surge is created which then decreases to a lower velocity as the sample advances through the column. For example, the carrier velocity may initially surge up to 5 m/s, but then decreases in velocity to about 1 m/s, then about 0.3 m/s.

Figure 3:
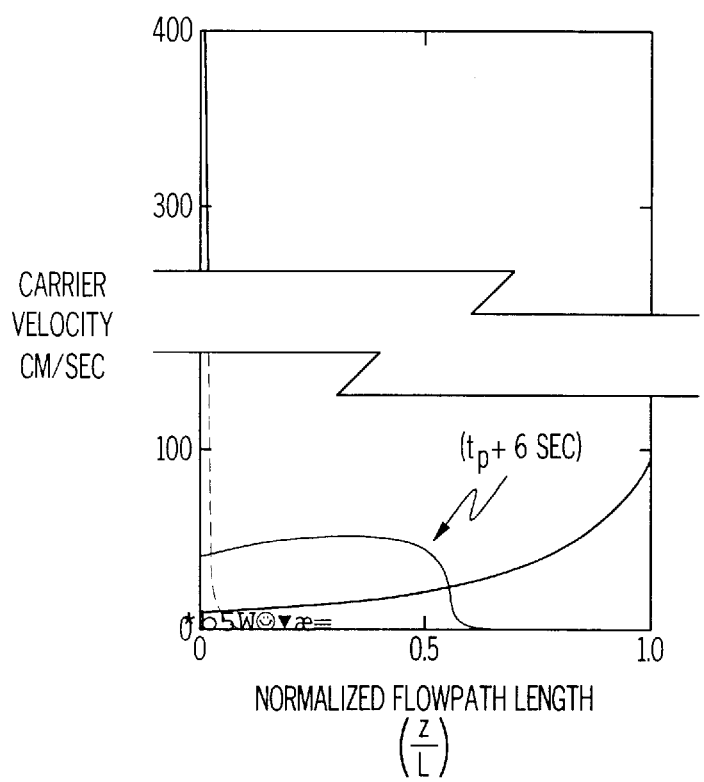
FIG. 3 is a graph illustrating the carrier velocity (cm/sec) versus normalized flowpath length after the step-increased pressurization step.

FIG. 3 is a graph illustrating the velocity surge which occurs with the step-increased pressurization method of the present invention. As can be seen, the carrier velocity under typical equilibrium conditions would have an exponentially rising curve. The dashed line curve represents the high carrier velocity resulting from the step-increased pressurization method of the present invention.

Also noted on the graph is the calculated carrier gas velocity versus distance which occurs approximately 5–6 seconds after the step-increased pressurization ($t_p$+6 sec). This curve shows that the mobile-phase velocity is approximately three times greater than that of the typical carrier velocities for the inlet region of an open tubular column.

Figure 4:
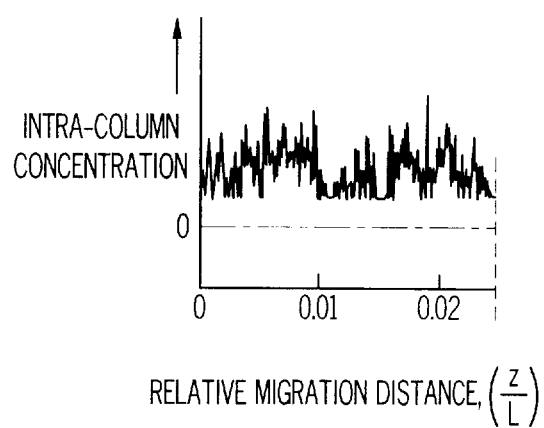
FIG. 4 is a graph illustrating the pre-separation which occurs at the inlet region of the column.

Solute motion after the step pressurization is such that especially narrow solute zones can be formed in the entrance region of the open tubular column, i.e., the various individual solutes which constitute the admitted sample are driven to near-stagnation axial motions and are efficiently distributed along the entrance portion of the open tubular column. FIG. 4 provides a typical illustration of the narrow zones formed after the pre-separation has taken place.

With the use of the method of the present invention, troublesome solutes and analytes in a sample can be more readily separated and analyzed. The method of the present invention is gentle and is not destructive to fragile compounds. Accordingly, compounds that are thermally labile, adsorptive, or which exhibit low vapor pressures should experience significantly improved gas chromatography transport and analysis capabilities. Because of the applied negative axial thermal gradient, the method may be used in the analysis of complex hydrocarbon mixtures, and more particularly, for turbine engine fuels, various organic effluents encountered with combustion emissions, multi-phase mixtures (containing gases, liquids, and solids), and numerous other types of complex environmental samples arising from the thermal decomposition of various organic substances.

It should be appreciated that the method of the present invention may also be used in field sampling applications where a wide range of sampling temperatures may be utilized. The specific device used for solute trapping can be a liquid coated tube, an open tube with an adsorptive inner surface, or an uncoated tube.

The method of the present invention also allows the inlet region of the column to be backflushed inline after each separation. Referring back to FIG. 1, after pre-separation has taken place, there is a small flow of gas in the injector region which is flowing in a backward direction (i.e., toward the inlet). To increase the velocity of this gas in a backward direction, the variable restrictor 30 is activated while the injection region 16 is still being maintained at a high temperature. This forces the carrier gas to move in a backward direction at a high velocity such that nonvolatile or low-volatility materials contained in the sample are removed through backflush vent 34. It should be noted that this backward flow of gas does not interrupt the flow of gas which carries the sample forward.

Thus, the backflushing technique also utilizes a step-increased pressurization in combination with the application of a thermal gradient in order to remove nonvolatile deposits from the inlet region, eliminating the need for frequent injection region maintenance.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A method for admitting and receiving a sample into a gas chromatographic column
   having an inlet region and an outlet region, wherein said sample travels in a direction from said inlet region to said outlet region, said method comprising:
      admitting said sample into said inlet region of said column at a first temperature, said inlet region containing a carrier gas which is at a first pressure;

rapidly heating said inlet region of said column to a second temperature greater than said first temperature such that a negative axial thermal gradient is imposed along the length of said column;

substantially instantaneously increasing the gas pressure at said inlet region to a second pressure greater than said first pressure such that the velocity of said carrier gas is increased and solutes constituting said sample are pre-separated into narrow zones along the inlet region of said column.

2. The method of claim 1 in which said column comprises an open tubular column.

3. The method of claim 1 in which said first pressure is from about 1 to about 3 abs. atm and said second pressure is from about 6 to about 9 abs. atm.

4. The method of claim 1 in which said first temperature is about 20° C. and said second temperature is from about 380° C. to about 480° C.

5. The method of claim 1 in which the velocity of said carrier gas is increased to about 5 m/s.

6. The method of claim 1 in which said inlet region is from about 20 cm to 2 meters in length.

7. The method of claim 1 further including the step of backflushing said inlet region of said column after said solutes constituting said sample are pre-separated by increasing the flow of gas in said inlet region in a backward direction such that non-volatile materials from said sample deposited in the inlet region are removed from said inlet region.

8. The method of claim 7 wherein the flow of gas in increased by increasing gas pressure in said inlet region.

* * * * *